United States Patent
Fields

(10) Patent No.: US 9,345,707 B2
(45) Date of Patent: May 24, 2016

(54) PROCESS FOR THE PRODUCTION OF AN ENRICHED NATURAL ANTIOXIDANT MIXTURE FROM A SINGLE SOURCE PLANT

(71) Applicant: Applied Food Sciences, Inc., Austin, TX (US)

(72) Inventor: Chrstine C. Fields, Janesville, WI (US)

(73) Assignee: Applied Food Sciences, Inc., Austin, TX (US)

(*) Notice: Subject to any disclaimer, the term of this patent is extended or adjusted under 35 U.S.C. 154(b) by 0 days.

(21) Appl. No.: 14/530,464

(22) Filed: Oct. 31, 2014

(65) Prior Publication Data

US 2015/0119408 A1    Apr. 30, 2015

Related U.S. Application Data

(60) Provisional application No. 61/898,362, filed on Oct. 31, 2013.

(51) Int. Cl.
| | |
|---|---|
| *A61K 31/522* | (2006.01) |
| *A61K 36/185* | (2006.01) |
| *A61K 31/198* | (2006.01) |
| *A61K 31/05* | (2006.01) |
| *A61K 31/216* | (2006.01) |

(52) U.S. Cl.
CPC .............. *A61K 31/522* (2013.01); *A61K 31/05* (2013.01); *A61K 31/198* (2013.01); *A61K 31/216* (2013.01); *A61K 36/185* (2013.01); *A61K 2236/00* (2013.01)

(58) Field of Classification Search
CPC ... A61K 31/522; A61K 31/05; A61K 31/216; A61K 31/198; A61K 36/185
USPC ....................................... 544/267
See application file for complete search history.

(56) References Cited

U.S. PATENT DOCUMENTS

2015/0068544 A1*   3/2015   Moldoveanu et al. ........ 131/352

* cited by examiner

*Primary Examiner* — Kristin Vajda

(57) ABSTRACT

A process for extracting antioxidants from a plant, including contacting a plant material from a guayusa plant for a first time with a solvent, thereby obtaining a first slurry, filtering said first slurry, thereby obtaining a first extract, contacting said plant material for a second time with said solvent, thereby obtaining a second slurry, filtering said second slurry, thereby obtaining a second extract, combining said first extract and said second extract, thereby generating an third extract containing at least antioxidants, xanthines, and amino acids, and substantially drying said third extract.

20 Claims, 1 Drawing Sheet

(Prior Art)

ABC Testing

Advanced Botanical Consulting & Testing, Inc.
1169 Warner Ave., Tustin, CA 92780, Phone: (714) 259-0364 Fax: (714) 259-0365

Client Sample ID: 5 Pyramid teabag with 2.5 g of Ilex Guayusa  Received Date: 07/05/2010
Product code: N/A
Lot#: LT127N
Lab Number: 056939                                             Report Date: 07/16/2010

| Analyses | Results |
| --- | --- |
| $ORAC_{hydro}$* | 658.97 µmol TE/g |
| $ORAC_{lipo}$* | 0.29 µmol TE/g |
| Total polyphenols (UV-Vis) | 40.10 mg/g |
| L-Theanine (HPLC) | 1.33 mg/g |
| Theobromine (HPLC) | 0.40 mg/g |
| Caffeine (HPLC) | 32.80 mg/g |
| Catechins (HPLC) | ND (<1mg/g) |
| EGCG (HPLC) | ND (<1mg/g) |

Method: J of Agric Food Chemistry, 2001; 49(10); 4619-4626, & J of Agric. Food Chem., 2003, 51 (11), 3273-3279, AUV203A, ALC550A, ALC129A, ALC127A

* The ORAC analysis provides a measure of the scavenging capacity of antioxidants against peroxyl radical, one of the most common reactive oxygen species found in the body. $ORAC_{hydro}$ reflects water-soluble antioxidant capacity. $ORAC_{lipo}$ reflects fat-soluble antioxidant capacity Trolox, a water-soluble Vitamin E analog, is used as the calibration standard and the ORAC result is expressed as micro mole Trolox equivalent (TE) per capsule.

Analyzed by: _____ Approved by: _____
             Chemist                         Wendi Wang, PhD, President

PROCESS FOR THE PRODUCTION OF AN ENRICHED NATURAL ANTIOXIDANT MIXTURE FROM A SINGLE SOURCE PLANT

STATEMENT OF PRIORITY

The present application claims priority to U.S. Provisional Application No. 61/898,362, titled "Process For The Production Of An Enriched Natural Antioxidant Mixture From A Single Source Plant" and filed Oct. 31, 2013.

TECHNICAL FIELD

The present disclosure relates to the field of therapeutic natural products and a process for producing an enriched extraction of a natural antioxidant mixture rich in cinnamic acids, catechins, amino acids and xanthines from a single source plant material, guayusa, which can be used to prevent a host of inflammatory diseases such as diabetes, cancer, heart disease, Alzheimer's and obesity as well as help treat ailments associated with poor glucose metabolism, endothelial dysfunction, oxidative stress, inflammation and cognitive decline.

BACKGROUND

*Ilex guayusa* is an Amazonian tree of the holly genus, native to the Ecuadorian Amazon Rainforest. The plant yields xanthenes such as caffeine. In addition to caffeine, guayusa also contains theobromine, a stimulant commonly found in chocolate and L-theanine, a glutamic acid analog found in green tee that has been shown to reduce physical and mental stress. See Kimura K, Ozeki M, Jeneja L, Ohira H (2007). "L-Theanine reduces psychological and physiological stress responses." Biol Psychol 74 (1): 39-45. doi: 10.1016/j.biopsycho.2006.06.006 (http://dxdoi.org/10.1016%2Fj.biopsycho.2006.06.006). PMID16930802 (//hwww.ncbi.nlm.nih.gov/pubmed/16930802).

Current approaches for the use of the guayusa plant include steeping the leaves and forming a beverage substrate (the "tea") as previously disclosed in http://www.stashtea.com/info/guayusa.aspx and http://www.runa.org/our-guayusa/. The finished beverage produced from both the tea leaves and the Ready to Drink ("RTD") beverages is described as a naturally caffeinated herbal infusion produced from the leaves of a holly tree. The finished beverage composition contains antioxidants, catechins, vitamins and amino acids at relatively low levels (Antioxidant and Compounds Analysis of Guayusa tea, "Lab Number: 056939". Advanced Botanical Consulting & Testing, Inc., 2010) as well as xanthines or caffeine as a natural sources of energy, FIG. 1.

Accordingly, there is a need to find natural remedies for inflammatory diseases and enhance cognitive function through the production of an extract which contains a specific ratio of actives that allow for effective nutritional formulation and dosage in a concentrated way to ensure product efficacy without having to consume large volumes of liquid.

In addition, there is a need for an extract or essence of the guayusa tea leaves with an enhanced finished product sensory profile and a shelf life extension. Specifically, a need exists for a masking agent stabilizing oxidative damage to the antioxidant content without bitterness in a finished tea based beverages (IFT 2013, Chicago, Ill. Presented by TEAWOLF).

Finally, there is need for a medicinal extract with the specific active ratio which provides for health benefits not yet seen or described by ingestion of the guayusa tea alone. See Antioxidant and Compounds Analysis of Guayusa tea, "*Lab Number:* 056939". Advanced Botanical Consulting & Testing, Inc., 2010. Suggestive of their role in disease prevention, the active compounds in the guayusa plant, once harvested and concentrated to the correct ratio as described within the disclosure, demonstrate and provide enhanced beneficial effects in human health.

SUMMARY OF THE INVENTION

According to one aspect, the present disclosure relates to a process for extracting antioxidants from a plant, including contacting a plant material from a guayusa plant for a first time with a solvent, thereby obtaining a first slurry, filtering said first slurry, thereby obtaining a first extract, contacting said plant material for a second time with said solvent, thereby obtaining a second slurry, filtering said second slurry, thereby obtaining a second extract, combining said first extract and said second extract, thereby generating an third extract containing at least antioxidants, xanthines, and amino acids, and substantially drying said third extract.

In another aspect, the present disclosure relates to an antioxidant mixture prepared by a process comprising the steps of: contacting a plant material from a guayusa plant for a first time with a solvent, thereby obtaining a first slurry, filtering said first slurry, thereby obtaining a first extract, contacting said plant material for a second time with said solvent, thereby obtaining a second slurry, filtering said second slurry, thereby obtaining a second extract, combining said first extract and said second extract, thereby generating an third extract containing at least antioxidants, xanthines, and amino acids, and substantially drying said third extract.

BRIEF DESCRIPTION OF THE DRAWINGS

The following FIGURE are included to illustrate certain aspects of the present invention, and should not be viewed as an exclusive embodiments. The subject matter disclosed is capable of considerable modification, alteration, and equivalents in form and function, as will occur to one having ordinary skill in the art and the benefit of this disclosure.

FIG. 1 is a prior art lab result, Antioxidant and Compounds Analysis of Guayusa tea, "Lab Number: 056939". Advanced Botanical Consulting & Testing, Inc., 2010.

DETAILED DESCRIPTION

Definitions

The term "filtration" is used to refer to either ultrafiltration or nanofiltration. In general, the "permeate" is the component that passes freely through the filter, while the "retentate" is the component that is retained by the filter.

The term "microfiltration" refers to processes that use filtration membranes having larger pore size than both ultrafiltration and nanofiltration. Microfiltration involves subjecting the antioxidant extract or eluate to filtration through a filter having a pore size of less than about 0.50 μM.

As used herein, the term "nanofiltration" refers to processes that use filtration membranes having a smaller molecular weight or pore size than those typically used in ultrafiltration processes. Like ultrafiltration, nanofiltration rejects a portion of the extract or eluate components above a certain molecular size while allowing those of a smaller size to pass through. Suitable nanofiltration membranes for use in the process disclosed herein are preferably made from polymers having a nominal molecular weight cut off of from about 700 Da to about 5000 Da (corresponding to pore sizes in the range of from about 17 A to about 40 A). Particularly preferred nanofiltration membranes are made from polymers having a nominal molecular weight cut off of from about 800 Da to about 2000 Da (corresponding to pore sizes in the range of from about 18 A to about 27 A). This pore size, in general, allows unoxidized phenolic compounds to pass through the membrane while retaining larger sized protein like compounds.

As used herein, the term "plant material" means species of guayusa (*Ilex guayusa*), preferably the tea leaves.

As used herein, the terms "antioxidant-containing eluate" and "antioxidant eluate" are used interchangeably to refer to the desired antioxidant-containing component collected after exposure to the adsorbent as described herein. Such adsorption step may be column adsorption, or any other adsorption means known to those having ordinary skill in the art.

As used herein, the term "nutrient-rich extract" means an extract having a nutrient concentration of at least about 5 times, and preferably at least about 15 times, the starting composition based on the High-Performance Liquid Chromatography ("HPLC") measurement, of the desired compounds (chlorogenic acids, xanthines, amino acids and flavonoids).

As used herein, the term "antioxidant containing retentate" means the amino acid-containing components remaining on the upstream side of the filter after ultrafiltration or nanofiltration. Such amino acid-containing retentates are used as the source of polyphenols, flavonoids, xanthines and other water soluble vitamins.

As used herein, the terms "amino acid-containing eluate," "amino acid eluate" and "amino acid rich extract" are used interchangeably to refer to the desired amino acid-containing components collected after exposure to the adsorbent as described herein such as the L-theanine or luecine. Such adsorption step may be column adsorption, or any other adsorption means known to those having ordinary skill in the art.

As used herein, the term "ultrafiltration" means a filtration method that uses an open filtration membrane with a pore size capable of allowing through molecules from at least about 10,000 Da to at least about 100,000 Da in molecular weight. Typically, ultrafiltration removes large molecular weight polysaccharides and proteins, but not oxidized phenolics.

As used herein, the term "water," means any of: deionized water, reverse osmosis water, distilled water, process water, ion exchange or mixtures thereof.

All amounts, parts, ratios and percentages used herein are by weight unless otherwise specified.

Process

The first step in one embodiment of the presently disclosed process disclosed herein involves blanching the leaves by contacting the plant material with boiling water, preferably greater than 80° C., for approximately 30 seconds. In some embodiments, this step may also utilize other leaf pretreatment methods such as steam blanching, citric acid blanching or a convention withering step. However, in preferable embodiments, optimum conditions are met with non withered leaves to avoid any un-necessary oxidation of the phytochemicals prior to extraction. The blanched leaves are then contacted with a solvent to obtain an extract comprising the soluble antioxidants (flavonoids and cinnamic acids), xanthines, and amino acids. The plant material used in the present disclosure is guayusa (*Ilex guayusa*), and more preferably the guayusa leaves (other *Ilex* species with the particular nutrients desired may also be used, i.e. *Ilex vomitoria*). The preferred extraction process involves steeping the guayusa leaves in and ethanol:hot water solution. The guayusa leaves are extracted using a 70:30 ethanol:hot water solution from about 70° C. to about 100° C. (from about 158 F. to about 212° F.), preferably from about 75° C. to about 90° C. (from about 167° F. to about 194° F.), and more preferably from about 80° C. to about 85° C. (from about 176° F. to about 185° F.), and a combined tea leaf to solvent ratio of about from 1:10 to about 1:20, i.e. for every 1 kg of guayusa leaves used, about 10 to 20 kg of solvent solution is used. Additionally, the extraction can be completed using a complete water extraction, supercritical extraction or similar however the yields of polyphenols and catechins and other active compounds will change.

The guayusa leaves are soaked in the solvent between approximately 60 minutes to approximately 240 minutes, after which the wet leaves are filtered out through one or more layers of cheese cloth, or other similar straining material, and the antioxidant extract is collected. The wet leaves may then be re-extracted numerous additional times (preferably two or three more times) with another volume of hot water or a water solvent mixture and soaked for about 60 minutes to about 120 minutes further. The leaves are again filtered out and the nutrient rich extract collected. The filtered nutrient extracts can then combined and are ready for further processing or the second nutrient rich extract can be further processes itself, then combined with the first for a finished extract with ideal product specifications.

Exposing Extract to Absorbent

In one embodiment, the nutrient rich extract resulting from the previous step is subsequently exposed to an adsorbent, which separates the desired compounds from other associated substances, such as the pectins and fiber. The result is a nutrient rich containing eluate that is substantially free of the aforementioned associated insoluble compounds and impurities. The preferred method of carrying out this adsorption step is column chromatography. However, any similar method of separation commonly known to those skilled in the art is acceptable. For example, the nutrient rich extract and adsorbent may be combined in a solvent medium and mixed thoroughly or through a multistage supercritical extraction process.

As previously mentioned, column chromatography is the preferred method to separate the desired extract from the other components in the nutrient rich extract. To separate via column chromatography, an inert column, preferably one made of glass or plastic, is first packed with an adsorbent or column packing. The adsorbent material may be any of a variety of hydrophobic cationic materials, however, polymeric resins, such as polyamides or polyclar are preferred. The column is then equilibrated with a solvent that is preferably water-soluble and does not form two phases when mixed with water. The solvent utilized in this phase of the process is preferably selected from water, ethanol, propylene glycol, glycerin, weak solutions of acetone, propanols, other like alcohols, and mixtures thereof. More preferably, the solvent comprises a mixture of water and ethanol. Still more preferably, the solvent mixture comprises less than about 80%, preferably less than about 70% ethanol, by weight of the solvent. In an alternate embodiment, the solvent comprises water.

Next, the nutrient rich extract is pumped through the column and the components that are not adsorbed, or poorly adsorbed, i.e. amino acids, will be the first class of components to elute with the solvent. As the solvent strength is increased, such as, for example, through the addition of more ethanol, more strongly adsorbed components are released from the adsorbent material in the column and elute with the solvent. This process allows for the separation of the desired materials and the production of an amino acid rich-containing eluate having a composition containing at least approximately 5% total amino acids.

Filtration of the Amino Acid-Containing Eluate

The amino acid containing eluate is then subjected to a filtration step, to remove additional high molecular weight material, such as polysaccharides, pectins and fiber, and further enrich the nutritional concentration of the eluate. As defined above, this filtration step may be either ultrafiltration or nanofiltration. Each of these filtration processes is set forth below Nanofiltration involves contacting the amino acid eluate with a nanofiltration membrane to provide a filtered nutrient-rich extract. Nanofiltration according to the present disclosure removes the higher molecular weight materials such as polysaccharides, pectins and fibers.

It is preferred that the nanofiltration step be carried out while the nutrient eluate is at a temperature of from about 30° C. to about 50° C. (about 86° F. to about 122° F.), preferably from about 35° C. to about 50° C. (about 95° F. to about 122° F.), and more preferably from about 45° C. to about 50° C. (about 113° F. to about 122° F.).

Efficient nanofiltration is typically achieved by warming the nutrient eluate after exposure to the adsorbent material and just prior to nanofiltration. The pressure at which nanofiltration is carried out is preferably sufficiently high to provide adequate flow of the nutrient eluate through the membrane to achieve the desired processing. However, the pressure is preferably not so high as to remove substantial amounts of water from the system. According to the present disclosure, nanofiltration is typically carried out under a hydrostatic pressure of from about 100 psi to about 300 psi, preferably from about 180 psi to about 280 psi, applied to the upstream side of the membrane.

Suitable nanofiltration membranes for use in the process of the present disclosure are made from polymers having a nominal molecular weight cut off of from about 700 Da to about 5000 Da (corresponding to pore sizes in the range of from about 17 A to about 40 A). Preferred nanofiltration membranes are made from polymers having a nominal molecular weight cut off of from about 800 Da to about 2000 Da (corresponding to pore sizes in the range of from about 18 A to about 27 A).

Suitable polymers are those that have less affinity for the desired polyphenol I flavonoid components in the nutrient eluate. Polymers such as cellulose and the like are usually suitable for making these nanofiltration membranes.

Typically, the resulting amino acid-rich extract is cooled to a temperature of about 16° C. (about 60° F.) or less.

Similar to nanofiltration, ultrafiltration involves contacting the nutrient eluate with an ultrafiltration membrane to provide a filtered nutrient-rich extract. Ultrafiltration uses an open filtration membrane with a pore size capable of allowing through molecules from at least about 10,000 Da to at least about 100,000 Da in molecular weight.

When utilizing ultrafiltration, the nutrient eluate can generally be filtered at a temperature of from about 30° C. to about 50° C. (about 86° F. to about 122° F.), preferably from about 35° C. to about 50° C. (about 95° F. to about 122° F.), and more preferably from about 45° C. to about 50° C. (about 113° F. to about 122° F.).

Once the nutrient eluate is subjected to one of the aforementioned filtration processes the nutrient composition obtained contains not less than approximately 10% total amino acids. The resulting amino acid-rich extract can now be enriched with the antioxidant polyphenols and xanthines removed during the initial extraction and separation steps by combining the two concentrated extracts, where evaporation and drying can produce a finished extract that contains no less than 30% chlorogenic acids, 10% xanthines and 5% amino acids, or 45 w/w % total nutrients. More specifically, the finished extract contains no less than 40% chlorogenic acids, 15% xanthines and 10% amino acids, or 65 w/w % total nutrients.

Using the Nutrient-Rich Extract

After subjecting the plant material to one of the foregoing embodiments, the resulting nutrient-rich extract may then be used to lower the glycemic response of a subject in a more effective way than prior guayusa compositional function (see Swanston-Flatt, S K et. Al Glycaemic effects of traditional European plant treatments for diabetes. Studies in normal and streptozotocin diabetic mice. Diabetes Res. 1989 February; 10(2):69-73) and assist in mood enhancement, provide a natural source of energy, decrease the risk of cardiovascular disease, enhance brain function, assist with weight management and lower oxidative stress.

The specific composition produced can provide an optimum source of natural energy that contains both an active element for enhanced metabolic function with its caffeine content while also assisting with glucose metabolism and regulation with the high level of chlorogenic acids. This ratio provides an ideal synergistic level of chlorogenic acids and caffeine to achieve effective weight loss benefits, whilst still shunting overactive insulin activity and hypertension typically associated with an increase in caffeine consumption.

Further, the specific composition may provide a masking agent to control the astringent, brackish or bitter taste when formulating, add a level of sweetness to the product or allow for increased shelf stability by protecting or stabilizing the finished formulation from oxidation.

EXAMPLES

Example 1

The following examples are illustrative of embodiments disclosed herein. Parts and percentages are by dry weight unless otherwise indicated. It should be noted that these examples describe a wide range of conditions, which together with the above descriptions, illustrate the present disclosure in a non limiting fashion.

About 400 g of commercial quality non withered guayusa tea leaves are extracted with about 1000 L of an ethanol: deionized water solution (70:30), at about 75° C. to about 85° C. (about 167° F. to about 186° F.) for approximately 120 minutes. The resulting slurry is filtered through two layers of muslin cloth and yields about 1200 g of crude tea extract. The residual leaves are re-extracted with deionized water under the foregoing conditions and again filtered through muslin cloth three more times. The tea extracts are combined and subjected to vacuum drying to concentrate the extract and remove additional impurities at about 80° C. until less than 3% moisture. The above semi solid extract is dissolved in ethanol then the top layer decanted. The top layer is then dried in a rotary drum dryer until less than 2% moisture. The final extract contains a profile of chlorogenic acids, catechins and caffeine for use as a nutritional ingredient in food and beverage applications.

The final extract phytochemical profile is as seen in Table 1:

TABLE 1

| Serial No. | Phyto-constituent | Assay in w/w % | Analysis method |
|---|---|---|---|
| 1 | Total Polyphenols | 35 ± 0.5 w/w % | Folin-Ciocalteu by spectrophotometric method |
| 2 | Total Chlorogenic acids | 32 ± 0.35 w/w % | LCMS/MS method |
| 3 | Caffeine | 26 ± 0.25 w/w % | LCMS/MS method |
| 4 | Theobromine | 0.0215 ± 0.005 w/w % | LCMS/MS method |
| 5 | L-Theanine | 0.011 ± 0.003 w/w % | LCMS/MS method |

Example 2

About 200 g of commercial quality guayusa tea leaves are extracted with about 550 L of an ethanol:deionized water solution (70:30), at about 75° C. to about 85° C. (about 167° F. to about 186° F.) for approximately 120 minutes. The resulting slurry is filtered through two layers of muslin cloth and yields about 1200 g of crude tea extract. The residual leaves are re-extracted with deionized water under the foregoing conditions and again filtered through muslin cloth. The tea extracts are combined and subjected to microfiltration via a 0.45 µM pleated filter (1.5 ft.sup.2, acrylic co-polymer on a polypropylene-polyester support). The resulting permeate is then subjected to nanofiltration using a Millipore® 1000 Dalton Molecular Weight Cut Off (MWCO) filter. The resulting permeate is then used to produce a clarified tea extract which contain the chlorogenic acids, xanthines and other phenols. The retentates from these filtrations, which contain the amino acids and glycosides, are combined to yield an amino acid-containing retentate with a volume of about 300 ml and about S0 Bx. This extract has an active concentration of about 600 mg/L. The nutrient rich extract is diluted with deionized water in a 1:1 ratio, and used as feed in the next step.

Amberlite XAD 16HP® (Rohm & Haas) is packed in a column (2.5 cm ID.times.75 cm height) to give a column volume of about 350 ml. The column is washed with about 4-5 column volumes of deionized water. The diluted nutrient extract from the foregoing extraction step is pumped into the column until breakthrough occurs (about 100 ml). The column is first eluted with deionized water to remove the non-phenolic materials including amino acids and other polysaccharides. When the eluate gives no precipitate or a clouding reaction with ethanol, the water elution is stopped. This eluate contains about 200 mg/L amino acids and about 10 mg/ml tea polysaccharides. It is then nanofiltered using a 1000 Dalton MWCO membrane to separate the high molecular weight non-phenolic materials from amino acids. The amino acid-rich extract is then added to the clarified polyphenol tea extract and further concentrated under vacuum until dry to remove any residual solvents and impurities. The finished substrate is then solubilized in a distilled solution and dried in a rotary evaporator to produce an extract of less than approximately 3% moisture.

The final extract phytochemical profile is as seen in Table 2:

TABLE 2

| Serial No. | Phyto-constituent | Assay in w/w % | Analysis method |
|---|---|---|---|
| 1 | Total Polyphenols | 47.1 ± 1.5 w/w % | Folin-Ciocalteu by spectrophotometric method |
| 2 | Total Chlorogenic acids | 41.5 ± 0.35 w/w % | LCMS/MS method |
| 3 | Caffeine | 36.8 ± 0.25 w/w % | LCMS/MS method |
| 4 | Catechins | 7.2 ± 0.05 w/w % | LCMS/MS method |
| 5 | L-Theanine | 1.40 ± 0.04 w/w % | LCMS/MS method |
| 6 | Theobromine | 0.266 ± 0.007 w/w % | LCMS/MS method |

Example 3

200 grams of non-withered Guayusa tea leaves are extracted with an Ethanol:water mixture (95:5) at 55° C. to about 65° C. The water to tea leaves ratio is about 15:1. This extraction is continued for about 2 hours, and the resulting nutrient dense extract is filtered using a filtration funnel with a waterman filtering paper. The residual tea leaves are then extracted twice more with an ethanol:water solvent at a ratio of 90:10, and this second and third nutrient extracts 2 and 3 are passed through filtration using whatman filter paper to remove any residual tea powder residue. The three nutrient extracts are combined, and the total active content in them is determined to be about 220 mg/L.

The combined extracts are send through a buchi rotary evaporator vacuum pump to concentrate the extract and remove any residual solvents. The semi-solid extract is completely dried using a savant speedvac vacuum system. The final extract provides a nutrient dense substrate containing the optimum combination of antioxidants and caffeine for use as a nutritional component in foods, beverages and supplements.

The final extract phytochemical profile is as seen in Table 3:

TABLE 3

| Serial No. | Analysis | Amount | Method |
|---|---|---|---|
| 1 | Total Polyphenols | 22.3 ± 1.5 w/w % | Folin-Ciocalteu by spectrophotometric method |
| 2 | Total Chlorogenic acids | 21.1 ± 0.35 w/w % | LCMS/MS method |
| 3 | Caffeine | 17.6 ± 0.15 w/w % | LCMS/MS method |
| 4 | Catechins | 1.5 ± 0.05 w/w % | LCMS/MS method |
| 5 | L-Theanine | 0.002 ± 0.04 w/w % | LCMS/MS method |
| 6 | Theobromine | 0.165 ± 0.007 w/w % | LCMS/MS method |

Example 4

Seven female subjects, ages 29-45, were given 300 mg of guayusa extract containing 42% chlorogenic acid, 16% xanthines and 12% amino acids orally for 3 weeks. Subjects were measured at the onset and upon final administration for Nuerotransmitter levels of Serotonin, GABA, Dopamine, Norepinephrine, Epinephrine, Glutamate and Creatinine Results demonstrate an increase in Serotonin and GABA levels by 22% and 26% respectively, and an increase in of Dopamine, Norephipephrine, Epinephrine by 12%, 11% and 15%. Glutamate and Creatinine levels remained unchanged.

Example 5

Two sets of six ready-to-drink tea beverages were prepared by steeping conventional green tea leaves in water at a 1:1 ratio for ten minutes, filtering, pasteurizing, then bottling. With one set, prior to bottling, 200 mg of guayusa extract was added that contained 32% chlorogenic acid, 16% xanthines and 5% amino acids and 30% total glycosides. Packaging was carried out in conventional 500 ml RTD glass bottles and sealed with PTFE screw lined caps. The tea beverages were stored for a period of 12 weeks in a temperature controlled light deprived container. One sample from each set was analyzed over the 12 weeks period for total flavonol glycoside concentration and total EGCG concentration.

Over the 12 weeks period, the control set containing no guayusa reduced total glycoside concentration by 37% and total EGCG concentration by 40% with most of the degration during the last two weeks of the study, week 10-week 12. Over the same 12 week period the six green tea beverages containing the 200 mg of guayusa extract per 500 ml seen an average decrease in total glycosides of 2% and a total average decrease in EGCG of 8%. In addition sensory scores completed on both sets indicated an increase in overall product taste as sweetness score by 92% of the sensory evaluations.

Although the present disclosure has been described with reference to specific embodiments, this description is not meant to be construed in a limited sense. Various modifications of the disclosed embodiments, as well as alternative embodiments of the disclosure will become apparent to persons skilled in the art upon the reference to the description of the present disclosure. It is, therefore, contemplated that the appended claims will cover modifications that fall within the scope of the disclosure.

What is claimed is:

1. A process for extracting antioxidants from a plant, comprising:
    contacting a plant material from a guayusa plant for a first time with a solvent, thereby obtaining a first slurry;
    filtering said first slurry, thereby obtaining a first extract;
    contacting said plant material for a second time with said solvent, thereby obtaining a second slurry;
    filtering said second slurry, thereby obtaining a second extract;
    combining said first extract and said second extract, thereby generating an third extract containing at least antioxidants, xanthines, and amino acids; and
    substantially drying said third extract.

2. The process of claim 1, wherein said plant material is non-withered guayusa leaves, thereby preventing loss of anti-oxidants.

3. The process of claim 1, wherein said plant material is guayusa leaves that are one of blanched or raw guayusa leaves.

4. The process of claim 1, further comprising contacting at least one of said first or second extract with an absorbent prior to combining said first and second extracts, thereby generating an amino acid containing eluate.

5. The process of claim 4, further comprising filtering the amino acid containing eluate via one of an ultrafiltration or nanofiltration.

6. The process of claim 1, wherein said plant material is ground up portions of said guayusa plant leaves.

7. The process of claim 1, wherein said solvent is an ethanol:deionized water solvent comprised of approximately a 70/30 ratio.

8. The process of claim 1, wherein the solvent is selected from the group consisting of water, ethanol, and mixtures thereof.

9. The process of claim 1, wherein said filtering is performed via a muslin cloth.

10. The process of claim 1, further comprising filtering said second extract for a second time prior to combining said second extract with said first extract.

11. An antioxidant mixture prepared by a process comprising the steps of:
    contacting a plant material from a guayusa plant for a first time with a solvent, thereby obtaining a first slurry;
    filtering said first slurry, thereby obtaining a first extract;
    contacting said plant material for a second time with said solvent, thereby obtaining a second slurry;
    filtering said second slurry, thereby obtaining a second extract;
    combining said first extract and said second extract, thereby generating an third extract containing at least antioxidants, xanthines, and amino acids; and
    substantially drying said third extract.

12. The antioxidant mixture of claim 11, wherein said plant material is non-withered guayusa leaves, thereby preventing loss of anti-oxidants.

13. The antioxidant mixture of claim 11, wherein said plant material is guayusa leaves that are one of blanched or raw guayusa leaves.

14. The antioxidant mixture of claim 11, wherein said process further comprises contacting at least one of said first or second extract with an absorbent prior to combining said first and second extracts, thereby generating an amino acid containing eluate.

15. The antioxidant mixture of claim 11, wherein said process further comprises filtering the amino acid containing eluate via one of an ultrafiltration or nanofiltration.

16. The antioxidant mixture of claim 11, wherein said solvent is an ethanol:deionized water solvent comprised of approximately a 70/30 ratio.

17. The antioxidant mixture of claim 11, wherein the solvent is selected from the group consisting of water, ethanol, and mixtures thereof.

18. The antioxidant mixture of claim 11, wherein the process further comprises filtering said second extract for a second time prior to combining said second extract with said first extract.

19. The antioxidant mixture of claim 11, comprising a composition of no less than 5% chlorogenic acids, 10% xanthines, and 1% amino acids.

20. The antioxidant mixture of claim 11, comprising a composition of no less than 10% chlorogenic acids, 10% xanthines, and 5% amino acids.

* * * * *